United States Patent
Bathija (10) Patent No.: US 11,598,762 B2
(45) Date of Patent: Mar. 7, 2023

(54) METHOD OF ANALYZING THE BOND STRENGTH OF CEMENT AND FORMATION WITH DISCRETE IMAGE ANALYSIS

(71) Applicant: Saudi Arabian Oil Company, Dhahran (SA)

(72) Inventor: Arpita Pal Bathija, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 50 days.

(21) Appl. No.: 17/231,343

(22) Filed: Apr. 15, 2021

(65) Prior Publication Data
US 2021/0325364 A1    Oct. 21, 2021

Related U.S. Application Data

(60) Provisional application No. 63/011,342, filed on Apr. 17, 2020.

(51) Int. Cl.
*G01N 33/38* (2006.01)
*G06T 7/00* (2017.01)

(52) U.S. Cl.
CPC .......... *G01N 33/383* (2013.01); *G06T 7/001* (2013.01); *G06T 2207/30132* (2013.01)

(58) Field of Classification Search
CPC ............... G01N 33/383; G01N 33/38; G01N 2223/427; G01N 2015/1445; G01N 15/00; G01N 2015/144; G01N 2223/649; G01N 24/081; G01N 23/046; G01N 2203/0092; G01N 2203/00; G01N 2291/02827;

(Continued)

(56) References Cited

U.S. PATENT DOCUMENTS

| 10,890,045 B2* | 1/2021 | Chenault | E21B 33/128 |
| 2018/0228700 A1* | 8/2018 | Catel | A61K 6/70 |
| 2019/0249516 A1* | 8/2019 | Riha | E21B 33/1204 |

OTHER PUBLICATIONS

Wilson et al. "The Tournemire industrial analogue: Reactive-transport modelling of a cement-clay interface" ResearchGate, https://www.researchgate.net/publication/257207722, May 2013, 19 pgs.

(Continued)

*Primary Examiner* — Daniel R Miller
*Assistant Examiner* — Eric Sebastian Von Wald
(74) *Attorney, Agent, or Firm* — Dinsmore & Shohl LLP (57) ABSTRACT

A method of analyzing a composite plug includes creating a composite plug, where the composite plug includes a formation layer, a cement layer, and an interface region between them, and the cement extends into the formation sample in the interface region. The method further includes imaging the composite plug to gather a series of discrete images, where each discrete image in the series depicts a cross section of the composite plug and the discrete images are taken at set increments throughout a depth of the composite plug. The method further includes analyzing each discrete image in the series of discrete images to determine a porosity measurement of each discrete image, determine a first and second boundary of the interface region from the porosity measurement of each discrete image, and determine a depth of the interface region by a number of discrete images between the first boundary and the second boundary.

20 Claims, 4 Drawing Sheets

(58) Field of Classification Search
CPC ... G01V 2210/6244; G06T 7/001; G06T 7/00; G06T 7/0002; G06T 7/0004; G06T 7/0008; G06T 7/11; G06T 7/174; G06T 7/187; G06T 2207/30132; G06T 2207/30108; G06T 2207/30168; G06T 2207/30116; G06T 2211/40; G06T 2207/10081; F16D 2250/0061; F16K 5/00; F16K 5/0673; F16K 5/0678; F16K 5/0684; G05B 2230/21; F05B 2230/211; G16K 5/18; Y10T 156/1361; C04B 2201/00; C04B 2201/50; C04B 2201/52
See application file for complete search history.

(56) References Cited

OTHER PUBLICATIONS

Wu "Experimental Study on the Influence of ITZ on the Durability of Concrete Made with Different Kinds of Blended Materials" Universiteit Gent, 2013-2014, 290 pgs.
Brand "Interfacial Transition Zone Composition and Bonding in Cementitious Materials With Asphalt-Coated Particles" Dissertation, 2015, 494 pgs.
Burnol et al. "Uncertainty in the reactive transport model response to an alkaline perturbation in a clay formation" ResearchGate, https://www.researchgate.net/publication/255201807, May 2006, 8 pgs.
Abyaneh et al. "Investigating into the diffusivity of concrete using a three dimensional multiphase model" ResearchGate, https://www.researchgate.net/publication/282073445, Sep. 2012, 10 pgs.
Promentilla et al. "Evaluation of Microstructure and Transport Properties of Deteriorated Cementitious Materials from Their X-ray Computed Tomography (CT) Images" MDPI, 2016, 16 pgs.
Varga et al. "Grout-Concrete Interface Bond Performance: Effect of Interface Moisture on the Tensile Bond Strength and Grout Microstructure" Constr Build Mater. May 2018 ; 170: 747-756. doi: 10.1016/j.conbuildmat.2018.03.076, 24 pgs.
Moda et al. "Analysis of the bond interface between selfadhesive resin cement to eroded dentin in vitro" PLOS One, Nov. 2018, 19 pgs.
Torsseter et al. "Potential Leakage Paths along Cement-formation Interfaces in Wellbores; Implications for CO2 Storage" ResearchGate, https://www.researchgate.net/publication/274025829, Dec. 2014, 10 pgs.
Scheele et al. "Accuracy of a non-invasive CT-based measuring technique for cement penetration depth in human tibial UKA" BMC Medical Imaging, https://doi.org/10.1186/s12880-019-0312-x, 2019, 8 pgs.
Opedal et al. "Experimental Study on the Cement-Formation Bonding" SPE 168138, 2014, 12 pgs.
Cui et al. "Porosity Characterization in Interfacial Transition Zone Using Dual CT Scans" ASTM Journal of Testing and Evaluation, Mar. 2017, 11 pgs.
Diamond "Considerations in image analysis as applied to investigations of the ITZ in concrete" Elsevier, Cement & Concrete Composites 23 (2001) 171-178, 8 pgs.
International Search Report and Written Opinion dated Jul. 19, 2021 pertaining to International application No. PCT/US2021/027461 filed Apr. 15, 2021, 17 pages.
Agbasimalo, N. et al. "Experimental Study of the Impact of drilling fluid contamination on the integrity of cement-formation interface", vol. 6: Materials Technology; Polar and Arctic Sciences and Technology; Petroleum Technology Symposium, American Society of Mechanical Engineers, Jan. 1, 2014, pp. 879-885.
Hao, H. et al. "Comparative study on cementation of cement-mudcake interface with and without mud-cake-solidification-agents application in oil & gas wells", Journal of Petroleum Science and Engineering, vol. 147, May 16, 2016, pp. 143-153.
Kjoller, C. et al. "Novel experimental/numerical approach to evaluate the permeability of cement-caprock systems", International Journal of Greenhouse Gas Control, Elsevier, Amsterdam, NL, vol. 45, Dec. 23, 2015, pp. 86-93.
Anonymous: "Formula—Wikipedia", Jun. 2, 2021.

* cited by examiner

METHOD OF ANALYZING THE BOND STRENGTH OF CEMENT AND FORMATION WITH DISCRETE IMAGE ANALYSIS

CROSS-REFERENCE TO RELATED APPLICATIONS

This application claims the benefit of U.S. Provisional Application No. 63/011,342 filed Apr. 17, 2020, the entirety of which is incorporated herein by reference.

BACKGROUND

The present disclosure relates to a method of analyzing the bond strength of cement. More specifically, the present disclosure is directed to a method of imaging a composite of cement and formation and analyzing the images to quantify the bond strength between the cement and formation.

BRIEF SUMMARY

According to the subject matter of the present disclosure, a method of analyzing a composite plug includes casting a cement on top of a formation sample and curing the cement to create a composite plug, where the composite plug includes a formation layer, a cement layer, and an interface region between the formation layer and the cement layer, and the cement extends into the formation sample in the interface region. The method further includes imaging the composite plug to gather a series of discrete images from a first point to a second point, where each discrete image in the series of discrete images depicts a cross section of the composite plug, the discrete images in the series of discrete images are taken at set increments throughout a depth of the composite plug, and the interface region is disposed between the first point and the second point. The method further includes analyzing each discrete image in the series of discrete images to determine a porosity measurement of each discrete image, determine a first and second boundary of the interface region from the porosity measurement of each discrete image, and determine a depth of the interface region by a number of discrete images between the first boundary and the second boundary.

According to the subject matter of the present disclosure, a method of assessing the bond strength of cement includes casting a cement on top of a formation sample and curing the cement to create a composite plug, where the composite plug includes a formation layer, a cement layer, and an interface region between the formation layer and the cement layer, and the cement extends into the formation sample in the interface region. The method further includes imaging the composite plug to gather a series of discrete images from a first point to a second point, where each discrete image in the series of discrete images depicts a unique horizontal cross section of the composite plug bounded by an outer perimeter of the composite plug, and the interface region is disposed between the first point and the second point. The method further includes analyzing each discrete image in the series of discrete images to determine a porosity measurement of each discrete image and determine a depth of the interface region from the porosity measurement of each discrete image, and assessing the bond strength between the cement layer and the formation layer based on the depth of the interface region.

According to the subject matter of the present disclosure, a method of analyzing a composite plug includes casting a cement on top of a formation sample and curing the cement to create a composite plug, where the composite plug includes a formation layer, a cement layer, and an interface region between the formation layer and the cement layer, and the cement extends into the formation sample in the interface region. The method further includes non-destructively imaging the composite plug with an X-ray Computed Tomography scan to gather a series of discrete images from a first point to a second point, where each discrete image in the series of discrete images depicts a cross section of the composite plug, the discrete images in the series of discrete images are taken at set increments throughout a depth of the composite plug, and the interface region is disposed between the first point and the second point. The method further includes analyzing each discrete image in the series of discrete images to determine a porosity measurement of each discrete image and determine a depth of the interface region as a number of discrete images between a first boundary of the interface region and a second boundary of the interface region, where the first boundary of the interface region is the boundary between the interface region and the cement layer, and the second boundary of the interface region is the boundary between the interface region and the formation layer.

Although the concepts of the present disclosure are described herein with primary reference to some specific cement and formation composites, it is contemplated that the concepts will enjoy applicability to any composite including a layer of cement and a layer of different material.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Cementing is a primary component of oil well drilling, operation, and abandonment. Cement may be injected into the annular space between an oil well casing and surrounding rock formations. Cement may also be used as one or more components of a plug used to seal a well during abandonment. If the cement bond is inadequate, it may result in leakage of one or more liquids from the producing or abandoned well. Therefore, improved methods for experimentally assessing the bond strengths of cements of different formulas is desired to improve the cement bond strength used in the field before integrating the cement in or around a well.

The present disclosure is directed to a method of analyzing cement bond strength that includes imaging a composite plug of cement and formation throughout the depth of the composite plug to generate a series of discrete images of the cross sections of the composite plug. Each discrete image in the series of discrete images is analyzed for porosity. Further investigating the change in porosity throughout the depth of the composite plug provides a quantitative assessment of the bond strength of the cement. Embodiments of the method of assessing cement bond strength will now be described and, whenever possible, the same reference numerals will be used throughout the drawings to refer to the same or like parts.

Figure 1:
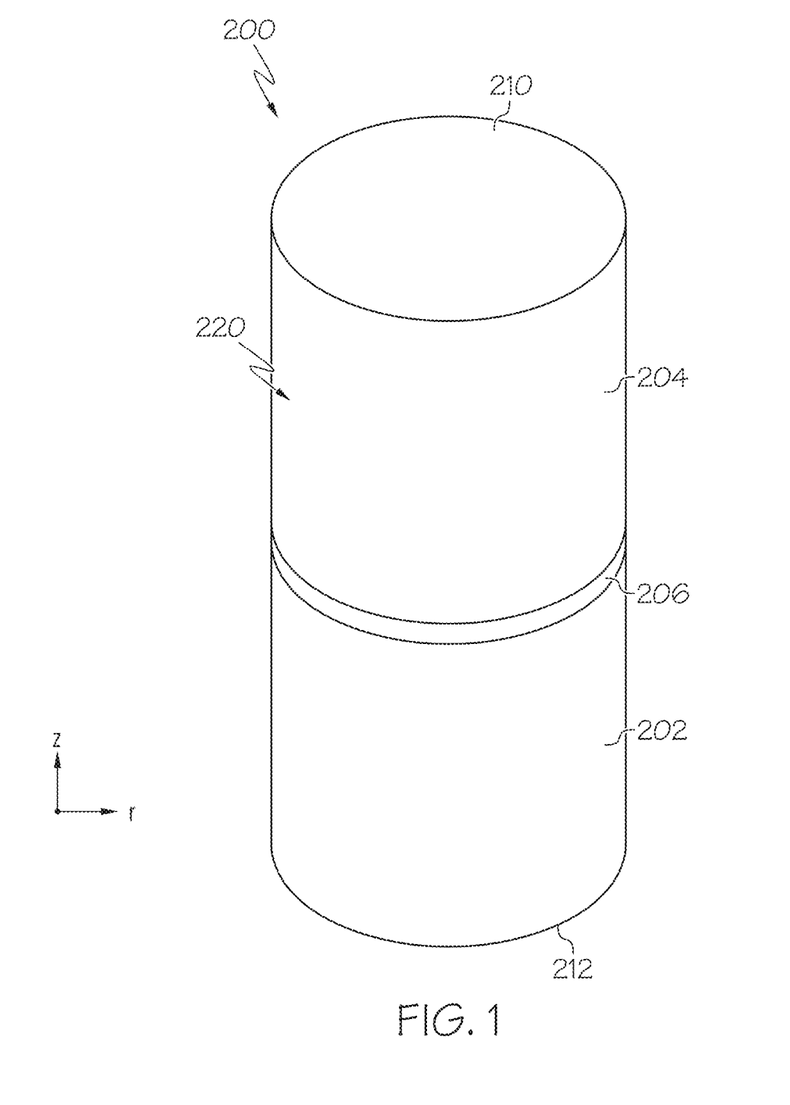
FIG. 1 schematically depicts a composite plug, according to one or more embodiments shown and described herein.

Referring now to FIG. 1, a composite plug 200 is schematically depicted. The composite plug 200 includes a formation layer 202 and a cement layer 204. The composite plug has a first end 210 and a second end 212. The first end 210 is part of the cement layer 204, and the second end 212 is part of the formation layer 202. The distance between the first end 210 and the second end 212 may span the entire depth of the composite plug 200. The first end 210 and the second end 212 may be parallel. At the boundaries of and between the formation layer 202 and the cement layer 204 is an interface region 206. The interface region 206 is the region of the composite plug 200 where the cement extends into the formation layer. In some embodiments, the composite plug 200 may be a cylinder. However, the composite plug 200 may be any shape that includes a depth and any size suitable for imaging and analysis. The formation sample used as the formation layer 202 may be any geological formation with which a particular cement formulation is expected to interact. The formation sample may also be any other porous material that it is desired to assess cement bond strength. In some embodiments, the formation sample is a sandstone sample.

Still with reference to FIG. 1, the term "longitudinal," as used throughout this disclosure, refers to a straight-line direction from the center of the first end 210 of the cement layer 204 to the center of the second end 212 of the formation layer 202. The longitudinal direction may extend in the z direction, as depicted in FIG. 1. Similarly, the term "depth," as used throughout this disclosure, refers to a distance in the longitudinal direction as described above. The term "horizontal," as used throughout this disclosure, refers to a straight-line direction orthogonal to the longitudinal direction. The horizontal direction may extend in the r direction, as depicted in FIG. 1. The outer edges of the composite plug 200 define a perimeter 220 of the composite plug.

Figure 2:
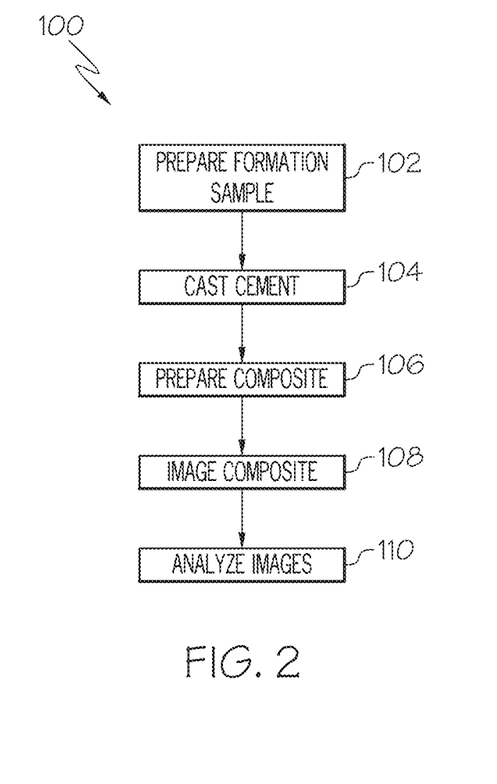
FIG. 2 schematically depicts a flowchart of the method of analyzing the bond strength of cement, according to one or more embodiments shown and described herein.

Referring now to FIG. 2, a flowchart of the cement bond strength assessment method 100 is schematically depicted. The cement bond strength assessment method 100 generally comprises the steps of preparing a formation sample (step 102), casting cement on the formation sample to form the composite plug (step 104), preparing a composite plug (step 106), imaging the composite plug (step 108), and analyzing the images (step 110). At step 102, the formation sample is initially prepared. The sandstone or other formation sample may be cored or harvested at a set cutting speed. In some embodiments, the formation sample may be a 1 inch by 1 inch cylinder. The cylindrical formation sample, for instance, may then be further prepared for experimentation by cutting a first longitudinal end and a second longitudinal end of the formation sample. The longitudinal ends of the formation sample may be cut to create flat longitudinal ends that are parallel with one another. For example, one longitudinal end may be the eventual second end 212 of the composite plug 200 (FIG. 1) and the other longitudinal end may be bonded with cement in steps 104 and 106. While a cylindrical formation sample is discussed in detail, in some embodiments, the formation sample may be of any suitable size or shape for testing purposes.

At step 104 a liquid cement mixture including cement, additives, and water may be cast onto the formation sample (e.g., onto one of the longitudinal ends of the formation sample) to create the composite plug 200. The liquid cement mixture may be cast on top of the formation sample in a cylindrical mold. In other embodiments, the mold may take any shape to match the shape of the formation sample. In other words, in embodiments, there should not be any open room between the interior wall of the mold and the formation sample.

At step 106, the composite plug 200 is prepared. The cement mixture is cured to form the composite plug 200 of cement and formation. The cement may be cured at any suitable temperature, pressure, and duration to obtain a hardened cement and a sufficient cement and formation bond. In some embodiments, the cement may be cured at 180 degrees Fahrenheit and 3000 psi for 3 days. Following curing, the mold may be removed from the composite plug 200. The composite plug 200 may be further prepared at step 106 by trimming the composite plug 200 to suitable dimensions. For instance, in some embodiments, the composite plug 200 may be trimmed to reach an overall length to diameter ratio of 2:1 for the entire composite plug 200. In some embodiments, the composite plug 200 may be trimmed to reach, at a minimum, an overall length to diameter ratio of 2:1. The composite plug 200 may also be trimmed to have equal amounts of the formation layer 202 and the cement layer 204. The composite plug 200 may then be further prepared for experimentation by cutting at least one of a first longitudinal end and a second longitudinal end of the composite plug 200. The longitudinal ends of the composite 200 may be cut so as to create flat longitudinal ends (i.e., the first end 210 and the second end 212) that are parallel with one another.

Still referring to FIG. 2, at step 108, the composite plug 200 is imaged with an imaging device. The imaging device may be any suitable imaging device to take cross-sectional images of the composite plug 200 throughout the depth of the composite plug 200. The imaging device may generate cross-sectional images of the composite plug 200 non-destructively. That is, the cross-sectional images of the composite plug 200 may be generated while maintaining the composite plug 200 intact. Put another way, the cross-sectional images of the composite plug 200 may be generated without altering the material or mechanical properties of the composite plug 200. This enables additional testing to be conducted on the composite plug 200 that may otherwise be unavailable if the composite plug 200 were cut, segmented, or altered to gather the cross-sectional images of the composite plug 200. In some embodiments, the composite plug 200 may be imaged with an X-ray Computed Tomography (CT) scan. The CT scan or other imaging device produces a series of discrete images of the cross sections of the composite plug 200. The series of discrete images are taken throughout the depth of the composite plug 200. Each discrete image is therefore of a unique horizontal cross section of the composite plug 200 along the depth of the composite plug 200. Therefore, each discrete image is a cross section of the composite plug 200 at a unique height of the composite plug 200 along the longitudinal axis of the composite plug 200 (e.g. in the direction of the z-axis of the coordinate axes of FIG. 1). In embodiments, each discrete image is a unique horizontal cross section of the composite plug 200 bounded by the perimeter 220 of the composite plug 200. In other words, a discrete image at a first height along the z-axis of FIG. 1 includes every radial point in the r-direction within the perimeter 220 of the composite plug 200 at the first height. The series of discrete images are taken at set increments through the depth of the composite plug 200. In embodiments, the set increments may be uniform, such that each slice in the discrete image of slices is an equal distance from its neighboring slices through the depth of the composite plug 200. In some embodiments, the set increments may be a predetermined spatial relationship that correlates a number of slices to a depth though the composite plug 200. That is, the incrementally spaced discrete images need not be uniformly spaced in all embodiments. As used herein, each discrete image may also be described as a "slice," and the series of discrete images may be described as a "series of slices."

Figure 3A:
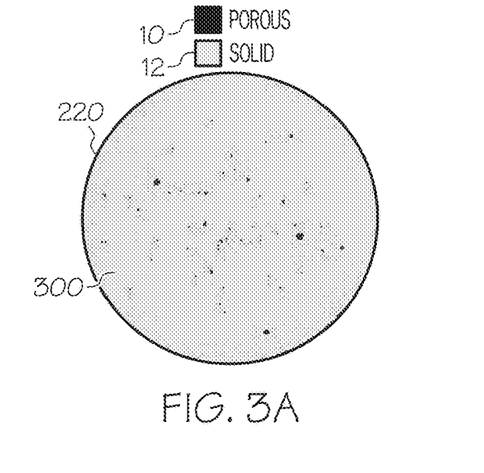
FIG. 3A schematically depicts a first discrete image in a series of discrete images of the cross sections of the composite plug of FIG. 1, according to one or more embodiments shown and described herein.
Figure 3B:
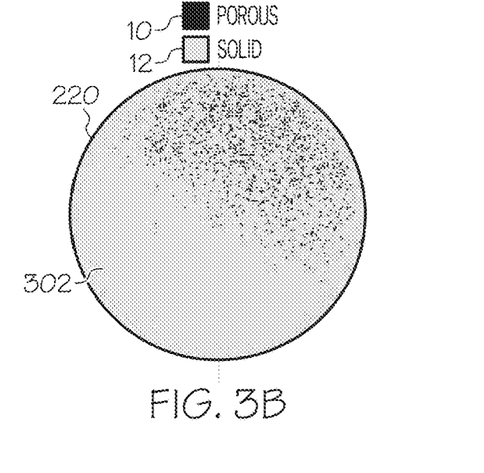
FIG. 3B schematically depicts a second discrete image in the series of discrete images of the cross sections of the composite plug of FIG. 1, according to one or more embodiments shown and described herein.
Figure 3C:
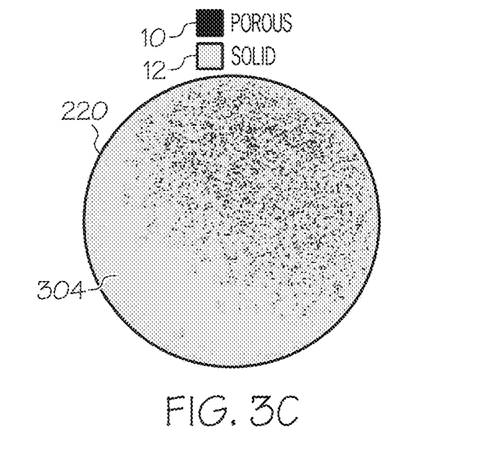
FIG. 3C schematically depicts a third discrete image in the series of discrete images of the cross sections of the composite plug of FIG. 1, according to one or more embodiments shown and described herein.
Figure 3D:
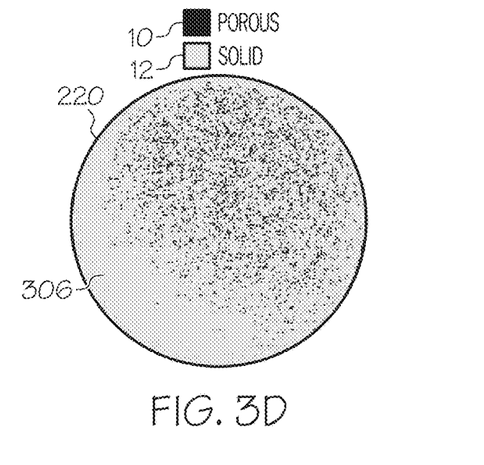
FIG. 3D schematically depicts a fourth discrete image in the series of discrete images of the cross sections of the composite plug of FIG. 1, according to one or more embodiments shown and described herein.
Figure 3E:
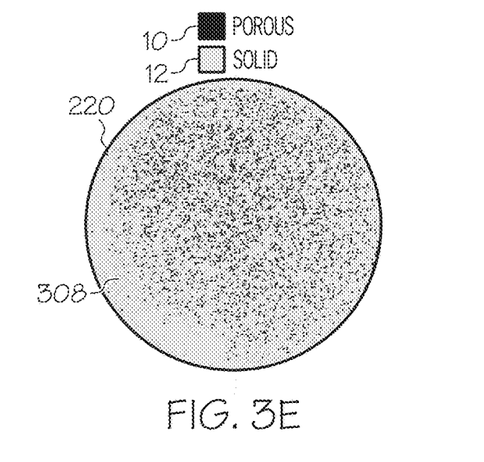
FIG. 3E schematically depicts a fifth discrete image in the series of discrete images of the cross sections of the composite plug of FIG. 1, according to one or more embodiments shown and described herein.
Figure 3F:
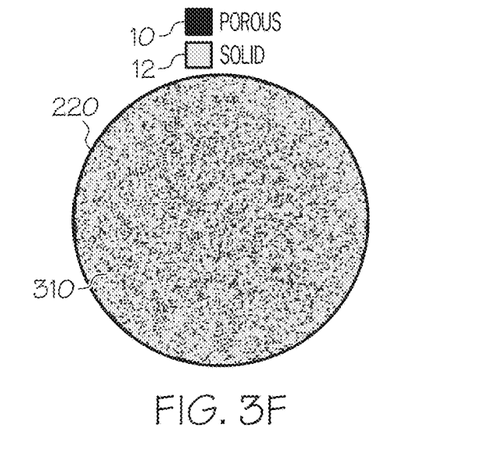
FIG. 3F schematically depicts a sixth discrete image in the series of discrete images of the cross sections of the composite plug of FIG. 1, according to one or more embodiments shown and described herein.

Referring now to FIGS. 3A-3F, example discrete images or slices throughout the depth of composite plug 200 imaged with a CT scan are depicted. FIG. 3A, specifically, depicts a cross section of the composite plug 200 in the cement layer 204. FIG. 3F, specifically, depicts a cross section of the composite plug 200 in the formation layer 202. FIGS. 3B-3E depict cross sections of the composite plug 200 in the interface region 206. Of the discrete cross-sectional images throughout the interface region 206 provided, FIG. 3B depicts a cross section of the interface region 206 closest to the cement layer 204, and FIG. 3E depicts a cross section of the interface region 206 closest to the formation layer 202. In other words, FIGS. 3A-3F span a depth of composite plug 200 from the cement layer 204 to the formation layer 202. FIGS. 3A-3F are merely representative discrete images from the entire series of discrete cross-sectional images. The entire series of discrete cross-sectional images span from a first point to a second point and the interface region 206 is disposed between the first and second point. In some embodiments, the first point may be on the first end 210 of the cement layer 204 and the second point may be on the second end 212 of the formation layer 202. In such embodiments, the series of discrete cross-sectional images may span the entire depth of the composite plug 200. In other embodiments, the first point and the second point may be disposed at locations between the first end 210 and the second end 212 in which that the interface region 206 remains between the first point and the second point.

The attenuation of the CT scan may be calibrated to porosity. Therefore, the porosity of a discrete cross section of the composite plug 200 may be determined from the attenuation value of the cross section. Porous regions of the cross section may have a lower attenuation than solid regions of the cross section. Therefore, a first discrete cross section of composite plug 200 with a lower attenuation than a second discrete cross section of composite plug 200 is more porous than the second cross section. The CT images and calibration between attenuation and porosity also allow for the pixelated depiction of solids and pores of a particular cross section of composite plug 200. For instance, in FIGS. 3A-3F, the black portions 10 of the images of discrete cross sections refer to porous regions of the cross sections, and the gray portions 12 of the images of discrete cross sections refer to solid regions of the cross sections.

Figure 4:
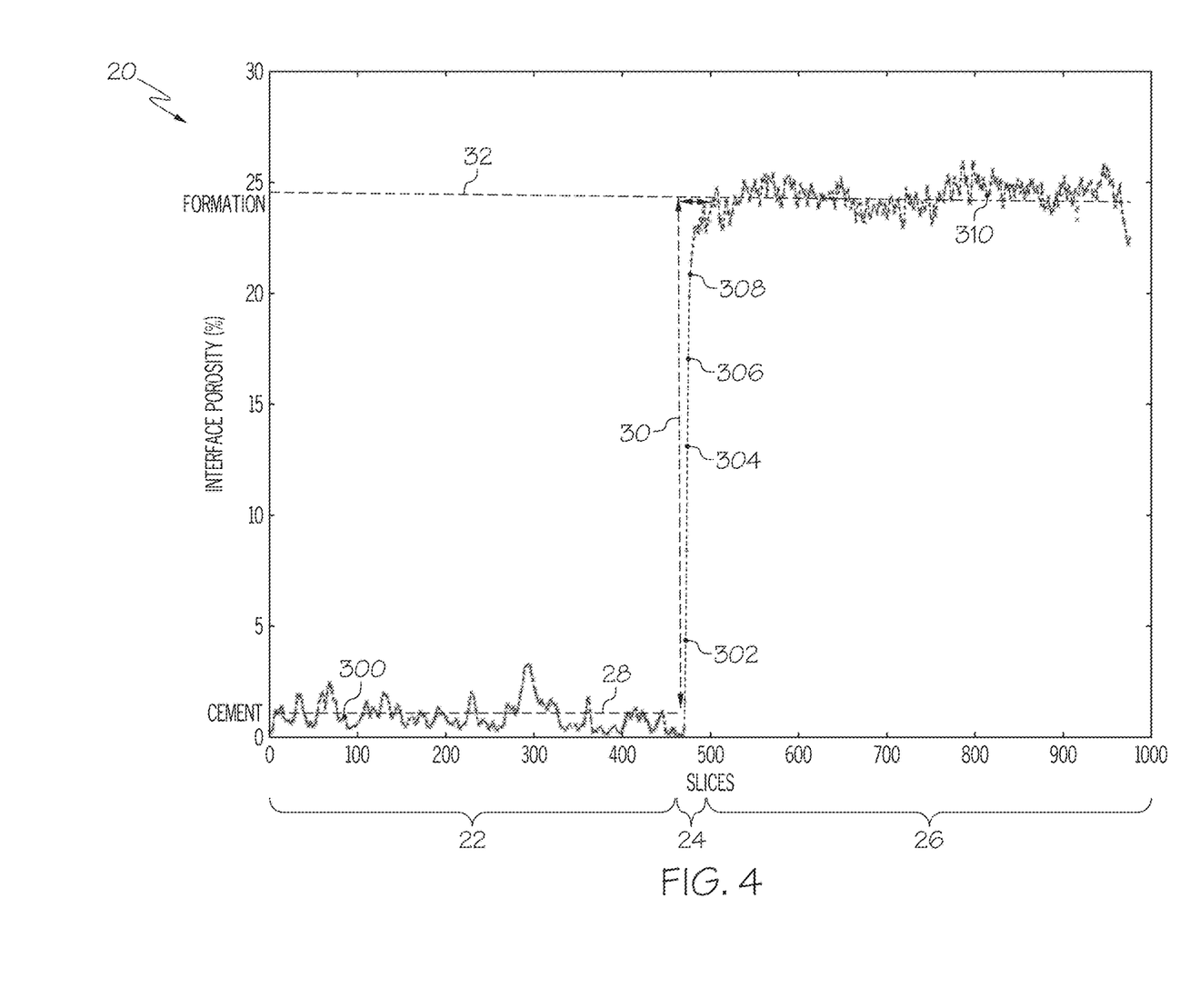
FIG. 4 schematically depicts a graphical plot and analysis of the porosity of each discrete image in the series of discrete images of the cross sections of the composite plug of FIG. 1, according to one or more embodiments shown and described herein.

Referring now to FIGS. 2-4, after the series of discrete images is collected, the series is analyzed. Each discrete image in the series is analyzed to determine a porosity measurement of each discrete image and determine a depth of the interface region 206 from the porosity measurement of each discrete image. For example, after the series of discrete images throughout the depth of the composite plug 200 is gathered, the series may be plotted in a graph 20 (FIG. 4) and further analyzed. The y-axis of graph 20 reports the porosity of each discrete image of a cross section of composite plug 200 in the series. The x-axis of graph 20 reports the slice number of each discrete image in the series. Region 22 of graph 20 corresponds to the cement layer 204 of composite plug 200, and region 26 of graph 20 corresponds to the formation layer 202. The cement layer 204 has a relatively low porosity, and the formation layer 202 has a relatively high porosity. The average porosity of cement layer 204 is reported by dashed line 28, and data point 300' of graph 20 corresponds to the cross section 300 depicted in FIG. 3A. In addition, the average porosity of the formation layer 202 is reported by dashed line 32, and data point 310' of graph 20 corresponds to the cross section 310 depicted in FIG. 3F.

Still referring to FIG. 4, region 24 of graph 20 corresponds to the interface region 206 of the composite plug 200. The boundaries of the interface region 206 may be found by analyzing the average porosities of the cement layer 204 and the formation layer 202, as well as the porosity of each discrete cross section, from the cement layer 204 to the formation layer 202, of the composite plug 200. The average porosities of the cement layer 204 and the formation layer 202 may be determined by averaging the porosity of a number of slices or cross sections within each layer. For instance, starting at the first end 210 of the cement layer 204 and extending toward the interface region, the porosity of a number of slices, where the number of slices is selected as being statistically representative of the entire cement layer 204, may be averaged. A similar method may be used from the second end 212 of the formation layer 202 to determine the average porosity of the formation layer 202. Once the average porosity of the cement layer 204 is determined, the beginning of the interface region 206 may be determined at the cross section that has a porosity greater than the average porosity of the cement layer 204, and is sequentially followed by cross sections whose porosities do not dip below the average porosity of the cement layer 204. The end of the interface region 206 may be determined at the first cross section, when analyzing the cross sections from the cement layer 204 to the formation layer 202, that has a porosity greater than or equal to the determined average porosity of the formation layer 202.

Once the boundaries of the interface region 206 are determined, one can then identify the total number of slices in the interface region 206. As the image slices are taken at set increments throughout the depth of the composite plug 200, the number of slices in the interface region 206 correlates to the depth of the interface region 206. Data point 302' of graph 20 corresponds to the cross section 302 depicted in FIG. 3B, data point 304' of graph 20 corresponds to the cross section 304 depicted in FIG. 3C, data point 306' of graph 20 corresponds to the cross section 306 depicted in FIG. 3D, and data point 308' of graph 20 corresponds to the cross section 308 depicted in FIG. 3F. As depicted in both the discrete cross sections shown in FIGS. 3A-3F and the plot of graph 20, porosity of a cross-sectional layer of composite plug 200, from a point in the cement layer 204, through the interface region 206, to a point in the formation layer 202, increases. In other words, porosity increases throughout the depth of composite plug 200, from the cement layer 204 to the formation layer 202. More specifically, porosity increases throughout the depth of interface region 206 from the boundary of the interface region 206 with the cement layer 204 to the boundary of the interface region 206 with the formation layer 202.

By further analyzing graph 20 of FIG. 4, the bond strength between the cement layer 204 and the formation layer 202 may be quantified using the formula (σ α N), where σ denotes bond strength, and N denotes the number of slices of the of the interface region 206. The first formula quantifies the cement bond strength by assessing the extent that the cement seeps into the pores of the formation. Based on the number of slices in the interface region 206, the depth of the interface region 206 and the extent of cement and formation bonding may be approximated. Based on the methods described above, the boundaries of the interface region 206 may be determined. For example, the interface region 206 may be determined to extend from slice 470 to slice 490. Thus, in this example N would equal 20. It has also been shown that the number of slices N of the interface region 206 may be approximately quantified by the formula $$\left(N \alpha \frac{k}{\mu}\right),$$

where k denotes the permeability of the formation and μ denotes the viscosity of the cement. That is, the number of slices N determined to be in the interface region 206 will generally increase with increasing permeability of the formation. This is generally because an increased permeability of the formation correlates to a greater amount of empty space in the formation that allows a greater amount of cement to seep into the formation. As also indicated, the number of slices N determined to be in the interface region 206 will generally increase with decreasing viscosity of the cement. This is generally because a decreased viscosity of the cement allows the cement to "flow" further into the pores of the formation. While the above formulas are particularly expressed as proportions, it should be appreciated that both formulas could be converted to equations with the collection of sufficient data. That is, the above proportions are applicable to composite plugs regardless of the specific cement and formation samples implemented in the composite plugs. With the collection of specific data, the proportions could be transitioned to equations including a known proportionality constants. For instance, with enough data collected on cement-Berea sandstone composite plugs, a proportionality constant specific to cement-Berea composite plugs could be solved for and the proportion $$\left(N \alpha \frac{k}{\mu}\right),$$

for instance, could be rewritten as the equation $$\left(N = a * \frac{k}{\mu}\right),$$

where a is a known proportionality constant.

In some embodiments, it may be desirable to determine the effect of one or more drilling fluids on the bond strength. In such embodiments of the disclosed method, the end of the formation sample that cement is cast on top of may be coated in one or more drilling fluids. The remainder of the disclosed method, in embodiments including a naked formation sample and a drilling fluid coated formation sample, may remain predominantly the same.

The quantified bond strength measurements gathered from the formula (σ α N) allow for easy comparison between different cement types and formation samples. For instance, as different cement compositions are formulated and considered for use in wells or other applications, the different compositions may be compared and analyzed with a greater degree of certainty. Similarly, the ability of a certain cement formulation to bond with different formation samples may be assessed. Additionally, effects of secondary factors, such as the use of different kinds of drilling fluid may be measured with greater certainty. The present disclosure provides the ability to determine which cement type bonds best with a particular formation and/or drilling fluid. The present disclosure also provides for experimental assessment of components, such as cement and drilling fluid, before their implementation in industry, providing the ability to identify less than optimal components and improve those components or find alternatives to the components before their use in the field.

EXAMPLES

Example 1

Example 1 is a first composite plug including cement cast on a Berea sandstone formation generated and tested using the methods described herein. Using the image analysis described herein, and generally including the steps of imaging the composite plug, generating a series of discrete images depicting unique horizontal cross sections of the composite plug, determining the porosity of each cross section, and determining a depth of the interface region based on a porosity of each cross section, the cement-Berea composite plug was found to have an interface region depth of 27 slices. The shear bond strength of the composite plug was measured by the integrated approach (Arpita P. Bathija and Roland Martinez, *An Integrated Approach to Understand the Failure Mechanism in Cement and Formation*, Society of Exploration Geophysicists 2535 (2020)) and was determined to be 31.8 MPa.

Example 2

Example 2 is a second composite including cement cast on a Torrey sandstone formation generated and tested using the methods described herein. Using the image analysis described herein, and generally including the steps of imaging the composite plug, generating a series of discrete images depicting unique horizontal cross sections of the composite plug, determining the porosity of each cross section, and determining a depth of the interface region based on a porosity of each cross section, the cement-Torrey composite plug was found to have an interface region depth of 9 slices. The shear bond strength of the composite plug was measured by the integrated approach (Arpita P. Bathija and Roland Martinez) and was determined to be 23.53 MPa.

Example 3

Example 3 is a third composite including viscous-cement cast on a Berea sandstone formation generated and tested using the methods described herein. Using the image analysis described herein, and generally including the steps of imaging the composite plug, generating a series of discrete images depicting unique horizontal cross sections of the composite plug, determining the porosity of each cross section, and determining a depth of the interface region based on a porosity of each cross section, the viscous-cement-Berea composite plug was found to have an interface region depth of 5 slices. The shear bond strength of the composite plug was measured by the integrated approach (Arpita P. Bathija and Roland Martinez) and was determined to be 23.47 MPa.

Analysis

The formulas ($\sigma \alpha N$) and $$\left(N\alpha\frac{k}{\mu}\right)$$

were experimentally verified using the above examples. It should be noted that the remaining physical (curing pressure, temperature, time, and the like) and chemical (cement additives) factors, besides the cement and formation samples selected to form the composite plugs, remained constant between the three composite plug examples. The permeability of Berea is 785 mD compared to a permeability of 2.74 mD in Torrey. Thus according to the formula $$\left(N\alpha\frac{k}{\mu}\right),$$

it follows that the cement-Berea composite plug possessed a greater number of slices in its interface region than the cement-Torrey composite plug. Moreover, as the viscous-cement possessed a larger viscosity than the standard cement sample, it also follows from the formula $$\left(N\alpha\frac{k}{\mu}\right)$$

that the cement-Berea composite plug possessed a greater number of slices in its interface region than the viscous-cement-Berea composite plug. It was additionally shown that the shear bond strengths of the composite plug specimens increased with the number of slices determined to be in the interface regions using the above-described imaging analysis. That is, the cement-Torrey composite plug, having a greater number of slices in its interface region than the viscous-cement-Berea composite plug, also displayed a greater shear bond strength as measured by the integrated approach. And the cement-Berea composite plug, having a greater number of slices in its interface region than the cement-Torrey composite plug, also displayed a greater shear bond strength as measured by the integrated approach. Accordingly, it is shown the cement-formation bond strength can be approximated by the number of cross sectional image slices determined to be in the interface region between the cement and formation using the above-described imaging analysis.

Further aspects of the invention are provided by the subject matter of the following clauses:

1. A method of analyzing a composite plug, the method comprising: casting a cement on top of a formation sample; curing the cement to create a composite plug, wherein: the composite plug comprises a formation layer, a cement layer, and an interface region between the formation layer and the cement layer; and the cement extends into the formation sample in the interface region; imaging the composite plug to gather a series of discrete images from a first point to a second point, wherein: each discrete image in the series of discrete images depicts a cross section of the composite plug; the discrete images in the series of discrete images are taken at set increments throughout a depth of the composite plug; and the interface region is disposed between the first point and the second point; and analyzing each discrete image in the series of discrete images to: determine a porosity measurement of each discrete image; determine a first and second boundary of the interface region from the porosity measurement of each discrete image; and determine a depth of the interface region by a number of discrete images between the first boundary and the second boundary.

2. The method of the preceding clause, wherein each discrete image in the series of discrete images depicts a unique horizontal cross section of the composite plug.

3. The method of any preceding clause, wherein each discrete image in the series of discrete images depicts a cross section of the composite plug at a unique height along a longitudinal axis of the composite plug.

4. The method of any preceding clause, wherein each discrete image in the series of discrete images is bounded by an outer perimeter of the composite plug.

5. The method of any preceding clause, wherein the composite plug is non-destructively imaged to gather the series of discrete images.

6. The method of any preceding clause, wherein the composite plug is imaged with an X-ray Computed Tomography scan.

7. The method of any preceding clause, wherein the attenuation of the X-ray Computed Tomography scan is calibrated to porosity.

8. The method of any preceding clause, wherein the first boundary of the interface region is the boundary between the interface region and the cement layer; and the second boundary of the interface region is the boundary between the interface region and the formation layer.

9. The method of any preceding clause, wherein the first boundary of the interface region is the first discrete image in the series of discrete images, analyzed from the cement layer to the formation layer, that has a porosity greater than an average porosity of the cement layer and is sequentially followed by discrete images having porosities that are greater than the average porosity of the cement layer.

10. The method of any preceding clause, wherein the second boundary of the interface region is the first discrete image in the series of discrete images, analyzed from the cement layer to the formation layer, that has a porosity greater than or equal to an average porosity of the formation layer.

11. The method of any preceding clause, further comprising assessing the bond strength between the cement layer and the formation layer.

12. The method of any preceding clause, wherein the bond strength is assessed with a formula (σ α N), wherein: σ denotes the bond strength; and N denotes the number of discrete images within the interface region.

13. The method of any preceding clause, wherein the number of discrete images within the interface region is a function of the permeability of the formation sample and viscosity of the cement $$\left(N\alpha\frac{k}{\mu}\right),$$

wherein: k denotes the permeability of the formation sample; and μ denotes the viscosity of the cement.

14. A method of assessing the bond strength of cement, the method comprising: casting a cement on top of a formation sample; curing the cement to create a composite plug, wherein: the composite plug comprises a formation layer, a cement layer, and an interface region between the formation layer and the cement layer, and the cement extends into the formation sample in the interface region; imaging the composite plug to gather a series of discrete images from a first point to a second point, wherein: each discrete image in the series of discrete images depicts a unique horizontal cross section of the composite plug bounded by an outer perimeter of the composite plug; and the interface region is disposed between the first point and the second point; analyzing each discrete image in the series of discrete images to determine a porosity measurement of each discrete image and determine a depth of the interface region from the porosity measurement of each discrete image; and assessing the bond strength between the cement layer and the formation layer based on the depth of the interface region.

15. The method of the preceding clause, wherein the bond strength is assessed with a formula (σ α N), wherein: σ denotes the bond strength; and N denotes the number of discrete images within the interface region.

16. The method of any preceding clause, wherein the discrete images in the series of discrete images are taken at set increments throughout a depth of the composite plug; and the depth of the interface region is determined by a number of discrete images of the series of discrete images between a first boundary of the interface region and a second boundary of the interface region.

17. A method of analyzing a composite plug, the method comprising: casting a cement on top of a formation sample; curing the cement to create a composite plug, wherein: the composite plug comprises a formation layer, a cement layer, and an interface region between the formation layer and the cement layer, and the cement extends into the formation sample in the interface region; non-destructively imaging the composite plug with an X-ray Computed Tomography scan to gather a series of discrete images from a first point to a second point, wherein: each discrete image in the series of discrete images depicts a cross section of the composite plug; the discrete images in the series of discrete images are taken at set increments throughout a depth of the composite plug; and the interface region is disposed between the first point and the second point; and analyzing each discrete image in the series of discrete images to determine a porosity measurement of each discrete image and determine a depth of the interface region by a number of discrete images between a first boundary of the interface region and a second boundary of the interface region, wherein: the first boundary of the interface region is the boundary between the interface region and the cement layer; and the second boundary of the interface region is the boundary between the interface region and the formation layer.

18. The method of the preceding clause, further comprising assessing the bond strength between the cement layer and the formation layer.

19. The method of any preceding clause, wherein the bond strength is assessed with a formula (σ α N), wherein: σ denotes the bond strength; and N denotes the number of discrete images within the interface region.

20. The method of any preceding clause, wherein: the first boundary of the interface region is the first discrete image in the series of discrete images, analyzed from the cement layer to the formation layer, that has a porosity greater than an average porosity of the cement layer and is sequentially followed by discrete images having porosities that are greater than the average porosity of the cement layer; and the second boundary of the interface region is the first discrete image in the series of discrete images, analyzed from the cement layer to the formation layer, that has a porosity greater than or equal to an average porosity of the formation layer.

For the purposes of describing and defining the present invention, it is noted that reference herein to a variable being a "function" of a parameter or another variable is not intended to denote that the variable is exclusively a function of the listed parameter or variable. Rather, reference herein to a variable that is a "function" of a listed parameter is intended to be open ended such that the variable may be a function of a single parameter or a plurality of parameters.

It is noted that recitations herein of a component of the present disclosure being "configured" or "programmed" in a particular way, to embody a particular property, or function in a particular manner, are structural recitations, as opposed to recitations of intended use. More specifically, the references herein to the manner in which a component is "programmed" or "configured" denotes an existing physical condition of the component and, as such, is to be taken as a definite recitation of the structural characteristics of the component.

It is noted that terms like "preferable," "typical," and "suitable" when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A method of analyzing a composite plug, the method comprising:
   casting a cement on top of a formation sample;
   curing the cement to create a composite plug, wherein:
      the composite plug comprises a formation layer, a cement layer, and an interface region between the formation layer and the cement layer; and
      the cement extends into the formation sample in the interface region;
   imaging the composite plug to gather a series of discrete images from a first point to a second point, wherein:
      each discrete image in the series of discrete images depicts a cross section of the composite plug;
      the discrete images in the series of discrete images are taken at set increments throughout a depth of the composite plug; and
      the interface region is disposed between the first point and the second point;
   analyzing each discrete image in the series of discrete images to:
      determine a porosity measurement of each discrete image;
      determine a first and second boundary of the interface region from the porosity measurement of each discrete image; and
      determine a depth of the interface region by a number of discrete images between the first boundary and the second boundary; and
   assessing the bond strength between the cement layer and the formation layer with a formula: $\sigma \propto N$, wherein:
      $\sigma$ denotes the bond strength; and
      N denotes the number of discrete images within the interface region.

2. The method of claim 1, wherein each discrete image in the series of discrete images depicts a unique horizontal cross section of the composite plug.

3. The method of claim 1, wherein each discrete image in the series of discrete images depicts a cross section of the composite plug at a unique height along a longitudinal axis of the composite plug.

4. The method of claim 1, wherein each discrete image in the series of discrete images is bounded by an outer perimeter of the composite plug.

5. The method of claim 1, wherein the composite plug is non-destructively imaged to gather the series of discrete images.

6. The method of claim 1, wherein the composite plug is imaged with an X-ray Computed Tomography scan.

7. The method of claim 6, wherein an attenuation of the X-ray Computed Tomography scan is calibrated to porosity.

8. The method of claim 1, wherein:
   the first boundary of the interface region is the boundary between the interface region and the cement layer; and
   the second boundary of the interface region is the boundary between the interface region and the formation layer.

9. The method of claim 1, wherein the first boundary of the interface region is the first discrete image in the series of discrete images, analyzed from the cement layer to the formation layer, that has a porosity greater than an average porosity of the cement layer and is sequentially followed by discrete images having porosities that are greater than the average porosity of the cement layer.

10. The method of claim 1, wherein the second boundary of the interface region is the first discrete image in the series of discrete images, analyzed from the cement layer to the formation layer, that has a porosity greater than or equal to an average porosity of the formation layer.

11. The method of claim 1, wherein the number of discrete images within the interface region is a function of a permeability of the formation sample and viscosity of the cement:

$$N \alpha \frac{k}{\mu},$$

wherein:
   k denotes the permeability of the formation sample; and
   µ denotes the viscosity of the cement.

12. A method of assessing the bond strength of cement, the method comprising:
   casting a cement on top of a formation sample;
   curing the cement to create a composite plug, wherein:
      the composite plug comprises a formation layer, a cement layer, and an interface region between the formation layer and the cement layer, and
      the cement extends into the formation sample in the interface region;
   imaging the composite plug to gather a series of discrete images from a first point to a second point, wherein:
      each discrete image in the series of discrete images depicts a unique horizontal cross section of the composite plug bounded by an outer perimeter of the composite plug; and
      the interface region is disposed between the first point and the second point;
   analyzing each discrete image in the series of discrete images to determine a porosity measurement of each discrete image and determine a depth of the interface region from the porosity measurement of each discrete image; and
   assessing the bond strength between the cement layer and the formation layer based on the depth of the interface region and a formula: $\sigma \propto N$, wherein $\sigma$ denotes the bond strength and N denotes a number of discrete images within the interface region.

13. The method of claim 12, wherein:
the discrete images in the series of discrete images are taken at set increments throughout a depth of the composite plug; and
the depth of the interface region is determined by the number of discrete images of the series of discrete images between a first boundary of the interface region and a second boundary of the interface region.

14. The method of claim 13, wherein:
the first boundary of the interface region is the first discrete image in the series of discrete images, analyzed from the cement layer to the formation layer, that has a porosity greater than an average porosity of the cement layer and is sequentially followed by discrete images having porosities that are greater than the average porosity of the cement layer; and
the second boundary of the interface region is the first discrete image in the series of discrete images, analyzed from the cement layer to the formation layer, that has a porosity greater than or equal to an average porosity of the formation layer.

15. The method of claim 12, wherein the number of discrete images within the interface region is a function of a permeability of the formation sample and viscosity of the cement:

$$N \alpha \frac{k}{\mu}$$

wherein:
k denotes the permeability of the formation sample; and
μ denotes the viscosity of the cement.

16. The method of claim 12, wherein:
the composite plug is non-destructively imaged with an X-ray Computed Tomography scan to gather the series of discrete images; and
an attenuation of the X-ray Computed Tomography scan is calibrated to porosity.

17. A method of analyzing a composite plug, the method comprising:
casting a cement on top of a formation sample;
curing the cement to create a composite plug, wherein:
the composite plug comprises a formation layer, a cement layer, and an interface region between the formation layer and the cement layer, and
the cement extends into the formation sample in the interface region;
non-destructively imaging the composite plug with an X-ray Computed Tomography scan to gather a series of discrete images from a first point to a second point, wherein:
each discrete image in the series of discrete images depicts a cross section of the composite plug;
the discrete images in the series of discrete images are taken at set increments throughout a depth of the composite plug; and
the interface region is disposed between the first point and the second point;
analyzing each discrete image in the series of discrete images to determine a porosity measurement of each discrete image and determine a depth of the interface region by a number of discrete images between a first boundary of the interface region and a second boundary of the interface region, wherein:
the first boundary of the interface region is the boundary between the interface region and the cement layer; and
the second boundary of the interface region is the boundary between the interface region and the formation layer; and
assessing the bond strength between the cement layer and the formation layer with a formula: σ α N, wherein:
σ denotes the bond strength; and
N denotes the number of discrete images within the interface region.

18. The method of claim 17, wherein:
the first boundary of the interface region is the first discrete image in the series of discrete images, analyzed from the cement layer to the formation layer, that has a porosity greater than an average porosity of the cement layer and is sequentially followed by discrete images having porosities that are greater than the average porosity of the cement layer; and
the second boundary of the interface region is the first discrete image in the series of discrete images, analyzed from the cement layer to the formation layer, that has a porosity greater than or equal to an average porosity of the formation layer.

19. The method of claim 17, wherein the number of discrete images within the interface region is a function of a permeability of the formation sample and viscosity of the cement:

$$N \alpha \frac{k}{\mu}$$

wherein:
k denotes the permeability of the formation sample; and
μ denotes the viscosity of the cement.

20. The method of claim 17, wherein an attenuation of the X-ray Computed Tomography scan is calibrated to porosity.

* * * * *